(12) United States Patent
Wagoner et al.

(10) Patent No.: US 7,214,925 B2
(45) Date of Patent: *May 8, 2007

(54) PATTERN METHOD AND SYSTEM FOR DETECTING FOREIGN OBJECT DEBRIS

(75) Inventors: Daniel E. Wagoner, Florissant, MO (US); Michael L. Taylor, Collinsville, IL (US); John C. Clayton, Genevieve, MO (US); John D. Fitts, St. Charles, MO (US); Greg L. Benfer, St. Charles, MO (US); Lynn E. Johnson, Warrenton, MO (US); Frank G. Speno, Glendale, MO (US)

(73) Assignee: The Boeing Company, Chicago, IL (US)

( * ) Notice: Subject to any disclaimer, the term of this patent is extended or adjusted under 35 U.S.C. 154(b) by 279 days.

This patent is subject to a terminal disclaimer.

(21) Appl. No.: 10/384,037

(22) Filed: Mar. 7, 2003

(65) Prior Publication Data

US 2003/0189178 A1    Oct. 9, 2003

Related U.S. Application Data

(63) Continuation-in-part of application No. 09/954,404, filed on Sep. 17, 2001.

(51) Int. Cl.
*G01N 21/64* (2006.01)

(52) U.S. Cl. ............ 250/221; 250/458.1; 250/302; 382/103; 382/141

(58) Field of Classification Search .......... 250/302, 250/338.1, 372, 221, 222.1; 116/200, 201; 473/198, 200, 353, 407; 29/720, 833; 382/103, 382/141; 361/760
See application file for complete search history.

(56) References Cited

U.S. PATENT DOCUMENTS

| | | | |
|---|---|---|---|
| 1,664,397 A | 4/1928 | Bens | |
| 3,534,589 A | 10/1970 | Gibbons et al. | |

(Continued)

FOREIGN PATENT DOCUMENTS

JP     08312627 A    * 11/1996

(Continued)

*Primary Examiner*—Thanh X. Luu
*Assistant Examiner*—Stephen Yam
(74) *Attorney, Agent, or Firm*—Ostrager, Chong, Flaherty & Broitman, P.C.

(57) ABSTRACT

A method of detecting a non-fixed object in a system (12) includes applying a light emitting or generating substance to multiple objects. The objects are illuminated with an object illuminator (13). At least one of the objects (10) is determined to be a nonmember within a known pattern of objects and is identified to be a non-fixed object in response to illumination of the objects.

16 Claims, 2 Drawing Sheets

U.S. PATENT DOCUMENTS

| | | | | |
|---|---|---|---|---|
| 3,745,566 A | * | 7/1973 | Johnson | 250/338.1 |
| 3,758,215 A | | 9/1973 | Paruolo et al. | |
| 3,839,639 A | * | 10/1974 | Hughes | 250/302 |
| 3,840,015 A | * | 10/1974 | Gain | 606/1 |
| 3,899,213 A | * | 8/1975 | Fantasia et al. | 250/301 |
| 3,911,733 A | | 10/1975 | Bhuta et al. | |
| 4,019,060 A | * | 4/1977 | Woodman | 250/461.2 |
| 4,549,206 A | * | 10/1985 | Suzuki et al. | 348/126 |
| 4,792,276 A | | 12/1988 | Krawiec et al. | |
| 5,281,826 A | * | 1/1994 | Ivancic et al. | 250/461.1 |
| 5,311,639 A | | 5/1994 | Boshier | |
| 5,370,387 A | | 12/1994 | Baker | |
| 5,417,529 A | * | 5/1995 | Volkmann et al. | 411/82 |
| 5,575,074 A | | 11/1996 | Cottongim et al. | |
| 5,662,533 A | * | 9/1997 | Chadwell | 473/353 |
| 5,934,852 A | * | 8/1999 | Stingl | 411/372.5 |
| 6,150,656 A | | 11/2000 | Garrity | |
| 6,480,394 B1 | * | 11/2002 | Feld et al. | 361/760 |
| 6,812,846 B2 | * | 11/2004 | Gutta et al. | 340/603 |
| 2002/0029032 A1 | * | 3/2002 | Arkin | 606/1 |

FOREIGN PATENT DOCUMENTS

| | | | | |
|---|---|---|---|---|
| JP | | 10280302 A | * | 10/1998 |
| JP | | 2000346024 A | * | 12/2000 |

* cited by examiner

PATTERN METHOD AND SYSTEM FOR DETECTING FOREIGN OBJECT DEBRIS

RELATED APPLICATION

The present application is a continuation-in-part (CIP) application of U.S. patent application Ser. No. 09/954,404 filed Sep. 17, 2001 entitled "A METHOD FOR DETECTING FOREIGN OBJECT DEBRIS", which is incorporated by reference herein.

TECHNICAL FIELD

The present invention relates generally to object detection methods, and more particularly to a method and system for detecting foreign object debris on an aircraft.

BACKGROUND OF THE INVENTION

Aircraft safety is an ongoing concern for aircraft producers. An unknown loose object on board an aircraft may cause an aircraft to malfunction or not operate as designed thereby decreasing safety of the aircraft. Unknown loose objects are referred to as foreign object debris (FOD) in the art. FOD are difficult to detect and many hours of searching for FOD occur during production of an aircraft, to assure the aircraft is free from loose objects, before the aircraft leaves a production facility or is operated. Moreover, because the detection of FOD relies almost solely on visual inspection, it can be subject to human error. Furthermore, confined nature of an aircraft structure hinders vehicle through inspection.

FOD are of various size and shape and can go undetected in large aircraft. A large aircraft has various cavities, pockets, and crevices that cause the process of detecting FOD to be difficult. For example, a small FOD item, such as a rivet or nut, lying in a dark crevice may go undetected during the search of a large aircraft. The larger the amount of undetected FOD the increased likelihood of an aircraft system malfunctioning.

A current method exists for locating a component that requires a supplemental restraining device on a portion of a gas turbine engine, as described in Garrity U.S. Pat. No. 6,150,656 entitled "Method of Assembly and Inspection for a Gas Turbine Engine", hereinafter referred to as Garrity. In Garrity a fluorescent material is applied to components of a gas turbine engine that require a supplemental restraining device before assembly thereof. An electromagnetic radiation is directed at the gas turbine engine to illuminate the fluorescent material. Upon illumination of the fluorescent material, a confirmation is made as to whether the components that requires a supplemental restraining device do in fact have a supplemental restraining device properly installed. As known in the art and as taught by Garrity, in order to properly install a supplemental restraining device, such as a lock-wire, to a component, the component must be fixed, otherwise the supplemental restraining device does not serve its intended purpose. Garrity unfortunately, is only directed at fixed components, on a gas turbine engine, that require proper installation of a supplemental restraining device as to prevent the components from becoming unfastened.

One known method of detecting foreign object debris is described in Wagoner et al., U.S. patent application entitled "A Method for Detecting Foreign Object Debris", hereinafter referred to as Wagoner. Wagoner teaches a method of detecting a non-fixed object, such as a loose fastener, within an aircraft. A light emitting substance is applied to the non-fixed object. A non-fixed object illuminator is used to illuminate the light emitting substance. The non-fixed object is detected due to the wavelength-specific light generated from illumination of the light emitting substance. Upon detection of the non-fixed object, the object is fastened or is determined to be FOD and is removed from the aircraft.

There are associated disadvantages with known FOD detecting methods. One disadvantage is that during inspection of an aircraft for FOD, using the known FOD detecting methods, some inspection areas can exist that are difficult to access or view and in some situations at least to some extent can not be inspected. Another disadvantage with exiting methods is that by continuously detecting FOD using an ultraviolet light source, eyestrain or ocular fluorescence can result that can lower a users ability to detect FOD. Furthermore, use of an ultraviolet lamp can be hazardous when there are defects in filters of existing FOD detecting systems that are used to eliminate more harmful ultraviolet wavelengths. Yet another disadvantage is that the existing systems use ultraviolet lamps that are large and can consume approximately 100 watts of power, thus generating a heat load and a potential burn or fire hazard.

There is a current desire to increase ability to detect FOD in a more effective and efficient manner than that used in Wagoner. It would therefore be desirable to develop an improved method for detecting FOD that reduces the time and costs involved in manufacturing of an aircraft which does not have the above-mentioned disadvantages with known existing techniques.

SUMMARY OF THE INVENTION

The foregoing and other advantages are provided by a method of detecting a non-fixed object in a system. The method includes applying a light emitting or generating substance to multiple objects. The objects are illuminated with an object illuminator. At least one of the objects is determined to be a nonmember within a known pattern of objects and is identified to be a non-fixed object in response to illumination of the objects.

One of several advantages of the present invention is that it provides an improved method for detecting non-fixed objects within an aircraft.

Another advantage of the present invention is that it provides an efficient method for detecting non-fixed objects within an aircraft.

Furthermore, the present invention provides a system that is capable of detecting non-fixed objects within areas that were traditionally difficult to access.

Moreover, the present invention synchronizes light from the object illuminator with the detector observing reflected light from the light emitting or generating substance. In so doing the present invention minimizes eyestrain, ocular fluorescence, and amount of average power consumed by the object illuminator, which in effect also reduces potential generation of a large heat load. By minimizing eyestrain and ocular fluorescence, a user's ability to detect FOD is increased. Also, the present invention by synchronizing light generation, a decreased frequency range of ultraviolet light is utilized allowing use of ultraviolet light frequencies that are relatively less harmful to a human eye.

In accordance with the above and other advantages of the present invention, production costs of an aircraft are reduced. Costs are reduced directly due to decreased time and energy in searching for non-fixed objects. Costs are also reduced indirectly as a result of potential decreases in post manufacturing costs due to aircraft malfunction caused by non-fixed objects going undetected. Aircraft quality and safety are also improved by increasing the probability that difficult to locate FOD will be identified.

The present invention itself, together with other attendant advantages, will be best understood by reference to the following detailed description, taken in conjunction with the accompanying figures.

BRIEF DESCRIPTION OF THE DRAWING

For a more complete understanding of this invention reference should now be had to the embodiments illustrated in greater detail in the accompanying figures and described below by way of examples of the invention wherein.

DETAILED DESCRIPTION OF THE PREFERRED EMBODIMENT

While the present invention is described with respect to a method and system for detecting non-fixed objects within an aircraft, the present invention may be adapted to be used for a variety of other components and systems including automotive vehicles, electronic or mechanical systems, machinery, or other components or systems that may require detection of a non-fixed object. The present invention may also be used in various production and manufacturing processes including before, during, and after assembly of a system. The present invention may also be applied in various types of inspection, such as in dye penetrant inspection of raw materials. In the following description, various operating parameters and components are described for one constructed embodiment. These specific parameters and components are included as examples and are not meant to be limiting.

Figure 1:
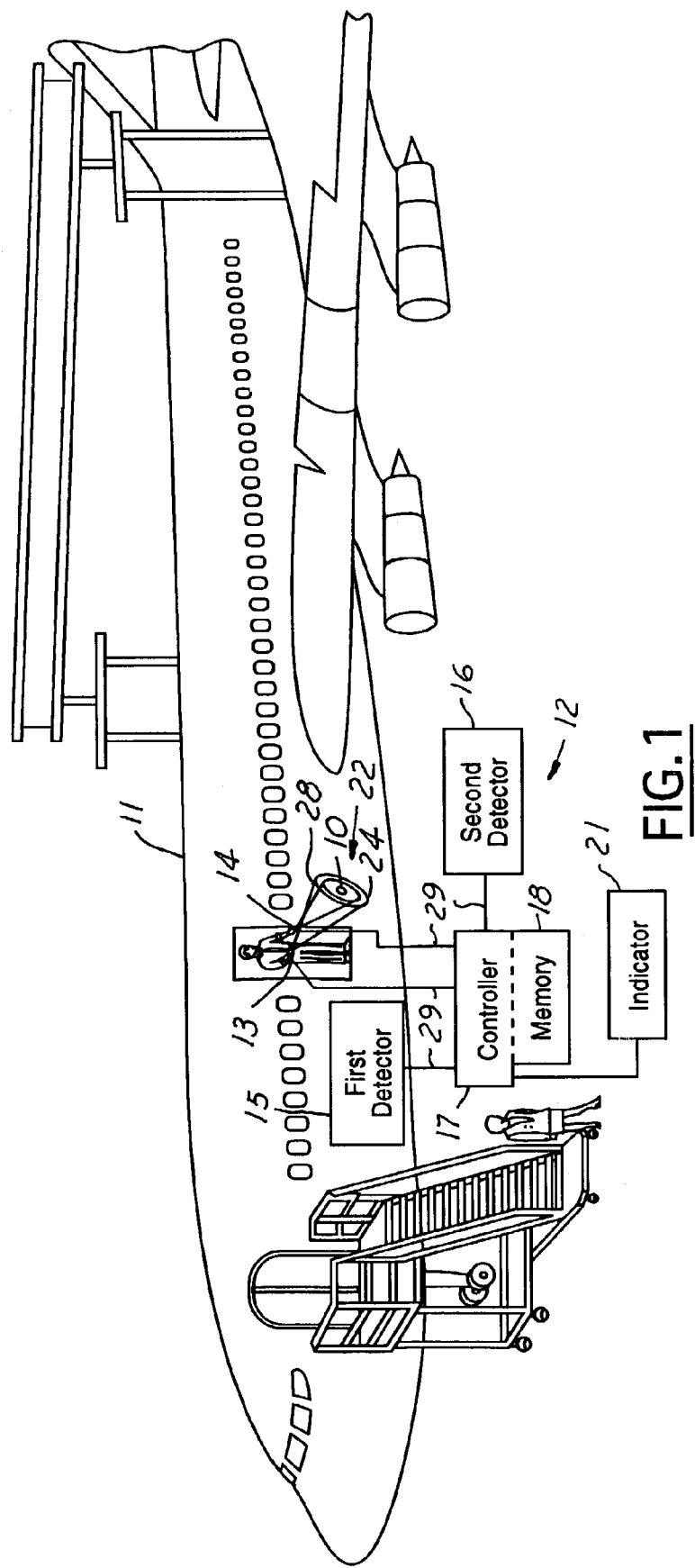
FIG. 1 is a representative illustration of implementing a method of detecting a non-fixed object in an aircraft using a foreign object debris detection system in accordance with a preferred embodiment of the present invention.

Referring now to FIG. 1, a representative illustration of implementing a method of detecting a non-fixed object 10 in an aircraft 11 using a foreign object debris (FOD) detection system 12 in accordance with an embodiment of the present invention is shown. The system includes a first object illuminator 13 and a second object illuminator 14, a first detector 15, a second detector 16, and a controller 17 having a memory 18. The object illuminators 13 and 14 illuminate the object 10. Reflected or generated illuminance from the object 10 is detected by the detectors 15 and 16. The controller 17 determines the object 10 to be a nonmember of a known pattern of objects. The object 10 may be determined to be FOD by the controller 17 or by the operator 20. An indicator 21 is electrically coupled to the controller 17 and indicates that the object 10 is a nonmember to a known pattern of objects. The object 10 may be: a tool, a system object, a non-system object, a loose or free moving object, a shaving, a chip, a free moving object, or other non-fixed object. A non-fixed object refers to an object that is loose or not fixed to the aircraft 11.

The first illuminator 13 may be any of the following: an ultraviolet light (black light), a fluorescent light, or a white light. The first illuminator may be in the form of a laser, a series of light emitting diodes (LEDs), or in some other form known in the art. The first illuminator 13 generates a first illumination beam 24 that illuminates an inspection area 22. The first illuminator 13 may be operated manually by the operator 20 or through the use of the controller 17 or an automated machine. The first illuminator 13 is powered as to illuminate areas throughout the aircraft 11 as to determine that an object is a nonmember of a known pattern of objects. The first illumination beam 24 has a predetermined frequency range that is preferably narrow and is within a range of the ultraviolet light spectrum that is less harmful to the human eye. The ultraviolet light spectrum that is less harmful to a human eye is approximately between 360 nm–400 nm, and is sometimes referred to as UVA The wavelength of the first illuminator 13 is selected to match the maximum absorption band of the light emitting or generating substance. The first illuminator 13 may be pulsed to match gating of the first detector 15 and the first detector 15 may be wavelength filtered to match an emission band of the light emitting or generating substance, thereby improving the signal-to-noise ratio of the resulting data.

The second illuminator 14 generates a second illumination beam 28 that may be in the form of visible light, such that an inspection area 22 of the aircraft 11 is illuminated sufficiently for image detection. The second illuminator 14 may be in the form of a strobe light, a series of LEDs, or in some other form known in the art. The operator 20 may use a portion of the system 12 to directly detect objects, such as the object 10, or may use the entire system 12. For example, the operator 20 may use the first illuminator 13 alone and directly detect objects or utilize the remaining components of the system 12 including the second illuminator 14, the detectors 15 and 16, and the controller 17 to detect objects, whereby the controller 17 indicates detection of an object via the indicator 21.

The detectors 15 and 16 may detect fluorescent, phosphorescent, luminescent, incandescent, photoluminescent, hotoluminescent, or other light emission known in the art. The detectors 15 and 16 may be infrared based, photoilluminescent based, or be of some other form of light detector known in the art. In a preferred embodiment of the present invention the first detector 15 is in the form of a first charge coupled device (CCD) camera, which is optical bandpass filtered to detect light within a predetermined frequency range and gated to correspond with or match the illuminator generating that light. The second detector 16 is in the form of a second CCD camera that detects light within approximately a visible light spectrum and is also gated to the illuminator producing that light. Gating refers to a method of controlling signals using combinational logic elements including a process of selecting portions of a wave between determined time intervals. Filtered refers to a method of selection within a predetermined frequency range. The predetermined frequency range is preferably narrow, within an approximate range to encompass the light spectrum that results from illumination of the light emitting or generating substance.

Although the detectors 15 and 16 are shown as separate components that may be a combined into a single detector or a portion of a single detector. The detectors may be CCD cameras, as stated above, or other form of detectors known in the art having bandpass filtering to detect frequencies within predetermined ranges.

The controller 17 is preferably a microprocessor-based controller such as a computer having a central processing unit, memory (RAM and/or ROM), and associated input and output buses. The controller 17 may store computer aided design (CAD) information so as to correlate known component locations in better detecting non-fixed objects that are nonmembers of a particular pattern.

The indicator 21 may be used to signal or indicate a nonmember identification signal in response to the object detection signals. The indicator 21 may generate video or audio signals, be as simple as an LED, may be in the form of a display, or may be some other type of indicator known in the art. The indicator 21 may simply indicate that FOD is present or may specify type and location of the FOD.

The illuminators 13 and 14, the detector 15 and 16, the controller 17, and the indicator 21 may be integrally formed into a single device or may be stand alone devices, as shown.

The illuminators 13 and 14 and the detectors 15 and 16 may be coupled to the controller 17 via cables 29, which may be in the form of fiber optic cables or other type of cables known in the art allowing the controller 17 to be at a remote location from the illuminators 13 and 14 and the detectors 15 and 16. The cables 29 in combination with the illuminators 13 and 14 or in combination with the detectors 15 and 16 may be in the form of a borescope, as known in the art. In one embodiment of the present invention, the operator 20 is at a remote location from the illuminators 12 and 14 and the detectors 15 and 16 and monitoring area 22 using the indicator 21. In an alternative embodiment, the detectors 15 and 16, along with any associated optics, are coupled to an opposite end of a borescope (not shown) as that of the controller 17. Remote object detection allows the present invention to detect non-fixed objects in difficult to access areas, such as when using steering capabilities of a borescope.

Figure 2:
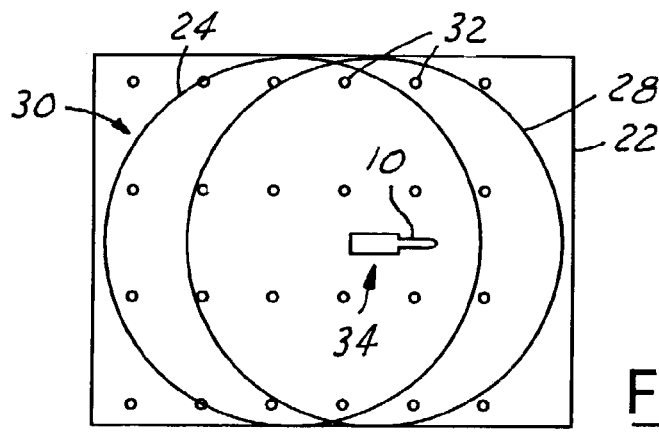
FIG. 2 is a representative illustration of a nonmember of a pattern of objects on the aircraft in accordance with a preferred embodiment of the present invention.

Referring now also to FIG. 2, representative illustration of the nonmember object 10 of a pattern of objects 30 on the aircraft 11 in accordance with a preferred embodiment of the present invention is shown. The nonmember object 10 has a light-emitting substance applied thereto, which is capable of being detected, by the operator 20 or the controller 17. For example, with respect to the aircraft 11, the light-emitting substance may be applied to at least a portion of any object that is intended or not intended to be fixed to the aircraft 11 including an object that may have a high probability of becoming loose or unfixed from the aircraft 11. The light emitting or generating substance may also be applied to fixed objects 32 in order to illuminate patterns of objects within the aircraft 11. Once an object has been subjected to the light-emitting substance, it may be better detected by the detectors 15 and 16 or by the operator 20. In accordance with an embodiment of the present invention, the operator 20 may walk around the aircraft 11 or may be at a remote location and utilize the system 12 to look for objects that are not fixed to the aircraft 11. The object 10 is in a location 34 on the aircraft 11.

Figure 3:
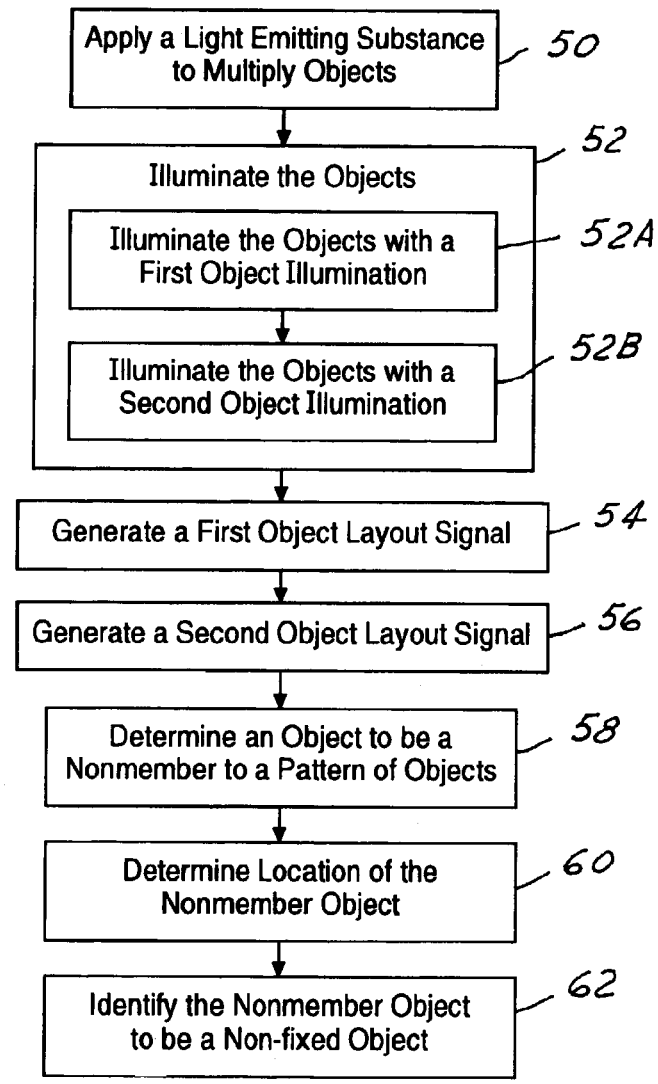
FIG. 3 is a flow chart illustrating the method of FIG. 1 in accordance with a preferred embodiment of the present invention.

Referring now to FIG. 3, a flow chart illustrating a method of detecting a non-fixed object in an aircraft in accordance with an embodiment of the present invention is shown. In accordance with the preferred method, a light emitting or generating substance is applied to at least a portion of the object 10 as well as to other system components and non system components, as generally indicated by reference number 50. The object 10 may be a system object or a non-system object. The light emitting or generating substance has a corresponding light emitting or generating frequency range, such that the light emitting or generating substance generates light approximately within the light emitting or generating frequency range and does not generate light outside of the light emitting or generating frequency range. The light emitting or generating frequency, for example, may be approximately 530 nm. Exemplary system objects include panstock items such as rivets, bolts, nuts, platenuts, Hi-loks, cotter pins, or other panstock items. Exemplary system objects may also include objects that are to be attached or fixed to the aircraft. A non-system object may be a tool, a shaving, a chip, or other object that is not to be attached or fixed to the aircraft.

The light emitting or generating substance may consist of any of the following: a coating, a paint, a dye, a stain, a powder, a tape, a fabric, a sheet or other light emitting or generating substance, which is known in the art. The light emitting or generating substance may also be produced from a material that is fluorescent, phosphorescent, luminescent, incandescent, photoluminescent, hotoluminescent, or other material that emits light. An example of a couple of fluorescent dyes that may be used are fluorescent dyes from ITW Dymon-Dykem product numbers DYX-163 and DYX-176. The light emitting or generating substance may be applied to the object 10 as well as other objects using any of the following processes: painting, dipping, spraying, marking, taping, coating, or other process known in the art. An example of a reflective tape that may be used is a tape from 3M Scotchcal™, which is identified by product number 7725404-7725414.

For example, as to differentiate between objects, fluorescent dye may be applied to panstock so as to detect and signify to the operator 20 that the detected object is a panstock item. Additionally, tools used to manufacture the aircraft may have reflective tape applied to them as to differentiate detected tools from panstock. Tools include pliers, screwdrivers, wrenches, air tools, and any other tools that are used in the production of an aircraft. The operator 20 may therefore upon detection of an object more effectively determine, in response to the type of reflection that is associated with a type of object, what appropriate action is required.

In accordance with the method, at least a portion of the object 10 is illuminated as well as other nearby objects, such as objects 32, as generally indicated by reference number 52. The objects are illuminated by the object illuminators 13 and 14, as generally indicated by reference numbers 52A and 52B, respectively. The object illuminators 13 and 14 are operated in order to illuminate the location 34 of the area 22. The object illuminators 13 and 14 may operate simultaneously or continuously, may be pulsed or clocked such that the first illuminator 13 operates for a determined time interval and the second illuminator 14 operates for a second time interval. In a preferred embodiment, the first illuminator 13 is synchronized to illuminate the objects 10 and 32 with light in a maximum absorption range of the light emitting or generating substance and not with light having other frequencies.

The detectors 15 and 16 in response to reflected or generated light from illumination of the objects 10 and 32 generate a first object layout signal and a second object layout signal, respectively, as generally indicated by reference numbers 54 and 56. The object layout signals contain illuminated object information such as object location, size, illuminance, and other object identification characteristics known in the art. In a preferred embodiment of the present invention the first object layout signal corresponds to object information generated from light generated by ultraviolet light on the light emitting or generating substance and the second object layout signal corresponds to object information generated from reflection of visible light on objects within the area 22. The first detector 15 may be gated and filtered to detect light within the light emitting or generating frequency range.

The object 10 is determined to be a nonmember within a known pattern of objects 32, by either the controller 17 or by the operator 20, in response to illumination thereof, as generally indicated by reference number 58. Known patterns may be stored within the memory 18. The patterns may consist of fixed object locations, relative distances between fixed objects, and type and style of the fixed objects. When an object, such as the object 10, is not within a proper location, having the proper size, a proper illuminance, or other object characteristic known in the art the operator 20 or the controller 17 may determine the object to be FOD. The controller 17 may in response to the object layout signals determine the object 10 to be a nonmember to the pattern 30 and generate a FOD signal, which is indicated by the indicator 21. The controller 17 also determines location of the object 10, as generally indicated by reference number 60.

In a simplified embodiment, the controller 17 in determining the object 10 to be a nonmember and in determining location of the object 10, may compare the first object layout signal with reference data, such as the above-mentioned patterns. In a more complex embodiment, the controller 17 may also superimpose location of the object 10, determined from the first object layout signal, onto the second object layout signal and use reference data to better determine location of the object 10. Video correlation techniques may be used to compare patterns and imaging data collected from the system 12 when determining whether the object 10 is a nonmember.

In another embodiment, when light emitting or generating material is removed from installed components, the controller 17 may also store information corresponding to multiple objects that are repeatedly falsely creating light. For example, when a light emitting or generating substance is intended to be removed from an object and is not completely removed, thus, remaining light emitting or generating material creates light and causes a false indication that the object is a nonmember. The controller 17 is therefore able to prevent false indications of objects being nonmembers again saving time in inspection of the aircraft 11.

The operator 20 may then determine that the object 10 is a non-fixed object to the aircraft 11, as generally indicated by reference number 62. The operator 20 then performs the appropriate action to either remove the non-fixed object, fasten the non-fixed object to the aircraft 11, to perform some other task known in the art, or determine that no action need be performed on the non-fixed object.

The above-described method may also be used after performing a production task such as drilling a hole, tightening an object, attaching an object, removing an object, or other production task. For example, when drilling a hole a light emitting or generating substance may be applied, such as a lubricant having a fluorescent powder, to a drill-bit or a surface being drilled such that the light emitting or generating substance sticks to or attaches to any shavings or chips that are created during drilling of the hole. The system 12 may then be used to detect the shavings or chips, such that the operator 20 may remove them as desired.

The present invention provides an efficient and improved technique for detecting non-fixed objects within an aircraft. The technique is quick, easy, and inexpensive to perform. The technique saves costs involved in production and manufacturing of an aircraft and post manufacturing costs caused by component malfunctions due to undetected non-fixed object.

The above-described apparatus, to one skilled in the art, is capable of being adapted for various purposes and is not limited to the following systems: automotive vehicles, electronic or mechanical systems, machinery, or other components or systems that may require detection of a non-fixed object. The above-described invention may also be varied without deviating from the spirit and scope of the invention as contemplated by the following claims.

What is claimed is:

1. A foreign object debris detection system comprising:
   a first object illuminator illuminating a plurality of objects having a light emitting or generating substance applied thereon;
   a first detector generating a first object layout signal of said plurality of objects in response to illumination of said plurality of objects; and
   a controller electrically coupled to said first detector and having a memory storing at least one object pattern, said controller determining an object to be a nonmember of at least one known pattern of member objects on a vehicular system, each of said known pattern having a plurality of reference member objects, in response to said first object layout signal.

2. A system as in claim 1 wherein said controller gates said first object illuminator with said first detector and wavelength filters said first detector to match generated light of said light emitting or generating substance.

3. A system as in claim 1 wherein wavelength of said first detector corresponds to a maximum absorption band of said light emitting or generating substance.

4. A system as in claim 1 further comprising:
   a second object illuminator illuminating said plurality of objects;
   said first detector generating a second object layout signal in response to illumination of said plurality of objects; and
   said controller superimposing location of said object on said first object layout signal in response to said first object layout signal and said second object layout signal to generate a superimposed signal.

5. A system as in claim 1 wherein said first object illuminator is a light selected from at least one of an ultraviolet light source, a fluorescent light source, or a white light source.

6. A system as in claim 1 wherein said controller in determining an object to be a nonmember of at least one known pattern compares said first object layout signal with reference data.

7. A system as in claim 1 further comprising:
   a second object illuminator illuminating said plurality of objects; and
   a second detector generating a second object layout signal in response to illumination of said plurality of objects;
   said controller superimposes location of said object on said first object layout signal in response to said first object layout signal and said second object layout signal to generate a superimposed signal.

8. A system as in claim 7 wherein said second object illuminator is a visible light source.

9. A system as in claim 7 wherein said controller in determining an object to be a nonmember of at least one known pattern compares said superimposed signal with reference data.

10. A system as in claim 7 wherein said first detector and said second detector are charge coupled device cameras.

11. A system as in claim 1 wherein said first detector is coupled to said controller via a fiber optic cable.

12. A system as in claim 1 wherein said first object layout signal is filtered to have only fluorescence wavelengths.

13. A system as in claim 1 wherein said first object layout signal is filtered to have only fluorescence wavelengths within a light emitting or generating frequency range of said light emitting or generating substance.

14. A system as in claim 1 wherein said light emitting or generating substance has an associated light emitting and generating substance maximum absorption frequency range and said object illuminator generates light in a frequency range that is approximately equal to said associated light emitting and generating substance maximum absorption frequency range.

15. A system as in claim 1 wherein said controller identifies said object to be a non-fixed object in response to said first object layout signal.

16. A system as in claim 1 wherein said controller determines light reflected from or generated by said object to be a false indication of a nonmember.

* * * * *